United States Patent
Tan et al.

(10) Patent No.: US 10,709,657 B2
(45) Date of Patent: Jul. 14, 2020

(54) HAIR-STYLING COMPOSITIONS COMPRISING A COMBINATION OF LATEX FILM-FORMING POLYMERS

(71) Applicant: L'OREAL, Paris (FR)

(72) Inventors: Siliu Tan, Westfield, NJ (US); Nghi Nguyen, Edison, NJ (US); Jim Singer, South Orange, NJ (US); Xian Zhi Zhou, Millburn, NJ (US)

(73) Assignee: L'OREAL, Paris (FR)

( * ) Notice: Subject to any disclaimer, the term of this patent is extended or adjusted under 35 U.S.C. 154(b) by 15 days.

(21) Appl. No.: 15/637,379

(22) Filed: Jun. 29, 2017

(65) Prior Publication Data

US 2019/0000746 A1 Jan. 3, 2019

(51) Int. Cl.
| | | |
|---|---|---|
| *A61Q 5/06* | (2006.01) | |
| *A61K 8/87* | (2006.01) | |
| *A61K 8/81* | (2006.01) | |
| *A61K 8/34* | (2006.01) | |
| *A45D 7/00* | (2006.01) | |

(52) U.S. Cl.
CPC ............ *A61K 8/87* (2013.01); *A61K 8/34* (2013.01); *A61K 8/8152* (2013.01); *A61Q 5/06* (2013.01); *A45D 2007/002* (2013.01); *A61K 2800/40* (2013.01); *A61K 2800/594* (2013.01)

(58) Field of Classification Search
None
See application file for complete search history.

(56) References Cited

U.S. PATENT DOCUMENTS

| | | | | | |
|---|---|---|---|---|---|
| 5,658,558 | A  * | 8/1997 | Schwartz | ......... | A61K 8/37 424/47 |
| 8,709,389 | B2 | 4/2014 | Schwarzwaelder | ...... | A61Q 5/06 424/70.1 |
| 9,788,627 | B2 * | 10/2017 | Tan | ......... | A61Q 5/06 |
| 9,789,050 | B2 * | 10/2017 | Tan | ......... | A61K 8/87 |
| 9,801,808 | B2 * | 10/2017 | Tan | ......... | A61K 8/04 |
| 9,814,668 | B2 * | 11/2017 | Tan | ......... | A61K 8/044 |
| 9,884,002 | B2 * | 2/2018 | Tan | ......... | A61K 8/8147 |
| 9,884,003 | B2 * | 2/2018 | Tan | ......... | A61K 8/8147 |
| 9,884,004 | B2 * | 2/2018 | Tan | ......... | A61K 8/87 |
| 2010/0189678 | A1 * | 7/2010 | Knappe | ......... | A61K 8/8152 424/70.16 |
| 2011/0142780 | A1 * | 6/2011 | Hentrich | ......... | A61K 8/8182 424/70.19 |
| 2012/0039819 | A1 * | 2/2012 | Nakatani | ......... | A61K 8/41 424/47 |
| 2013/0068243 | A1 | 3/2013 | Birkel et al. | | |
| 2015/0004114 | A1 | 1/2015 | Tan et al. | | |
| 2015/0004115 | A1 * | 1/2015 | Tan | ......... | A61K 8/8147 424/70.13 |
| 2015/0004116 | A1 | 1/2015 | Tan et al. | | |
| 2015/0004117 | A1 * | 1/2015 | Tan | ......... | A61K 8/87 424/70.16 |
| 2015/0004118 | A1 * | 1/2015 | Tan | ......... | A61K 8/8147 424/70.16 |
| 2015/0004119 | A1 | 1/2015 | Tan et al. | | |
| 2015/0004120 | A1 | 1/2015 | Tan et al. | | |
| 2015/0004121 | A1 | 1/2015 | Tan et al. | | |
| 2015/0004122 | A1 | 1/2015 | Tan et al. | | |
| 2015/0004123 | A1 | 1/2015 | Tan et al. | | |
| 2015/0004124 | A1 | 1/2015 | Tan et al. | | |
| 2016/0175206 | A1 | 6/2016 | Tan et al. | | |
| 2016/0184195 | A1 | 6/2016 | Tan et al. | | |

FOREIGN PATENT DOCUMENTS

| | | | |
|---|---|---|---|
| WO | WO-2016100433 | A2 | 6/2016 |
| WO | WO-2016100436 | A2 | 6/2016 |

OTHER PUBLICATIONS

DAITOSOL 5000 AD (Year: 2014).*
DIATOSOL 5000SJ (Year: 2014).*

* cited by examiner

*Primary Examiner* — Jyothsna A Venkat
(74) *Attorney, Agent, or Firm* — Polsinelli PC

(57) ABSTRACT

The instant disclosure relates to hair styling compositions and products comprising the hair styling compositions. The hair styling compositions include: one or more soft latex film-forming polymers having a glass transition temperature (Tg) of less than 35° C. or less; one or more hard latex film-forming polymers having a glass transition temperature (Tg) of 35° C. or more; less than 15 wt. % of water; and at least 80 wt. % of one or more organic solvents, wherein the composition has a shear viscosity of up to about 70 cP at 23° C. The compositions may further comprise one or more propellants, and are useful in products such as aerosol hair sprays, pump hair sprays, hair mousses, hair foams, hair gels, etc. The disclosure further relates to methods for styling the hair using the compositions and products.

6 Claims, No Drawings

HAIR-STYLING COMPOSITIONS COMPRISING A COMBINATION OF LATEX FILM-FORMING POLYMERS

FIELD OF THE DISCLOSURE

The present disclosure relates to hair-styling compositions comprising a combination of hard and soft latex film-forming polymers. The compositions are useful in products for styling hair, such as aerosol hair sprays, pump hair sprays, hair mousses, hair foams, hair gels, etc.

BACKGROUND

Traditional hair-styling products on the cosmetic market appear in various forms.

They range anywhere from solutions, foams, gels, creams, waxes, mousses, sprays, serums, to aerosols and can impart a variety of levels of protection (or damage) to the hair depending on the state of the hair and the components of the product. These types of products often include water soluble film-forming polymers. Depending on the chemical make-up of these polymers, they may be either soluble in water, or they may be water insoluble polymers which are made water soluble via various chemical modifications, such as neutralization. Solutions comprising these polymers tend to be viscous, i.e. as the concentration of the polymer increases, viscosity builds up rapidly. Translated to styling applications, as the solvent evaporates, the polymer solution becomes thicker on the hair surface, resulting in a sticky or tacky film. These products also tend to exhibit problems with product spreadability, hair manageability, and low degree of humidity resistance which is particularly a problem in hot and humid locations.

Latex polymers have been used in cosmetic products, for example, to provide extended-wear properties to the cosmetic product (e.g. mascara, eyeliner, nail polish) into which they are formulated. Some known compositions include one latex polymer.

For example, U.S. Pat. No. 6,126,929 describes a composition comprising a dispersion of a latex film former, optionally with a plasticizer, and a non-film-forming particle not capable of being film-formed. U.S. Pat. No. 4,710,374 describes a composition comprising cationic polymers, a surfactant, and an anionic latex. U.S. Pat. No. 7,740,832 describes a composition comprising at least one non-latex polymer and an anionic, cationic or amphoteric fixing polymer. U.S. Pat. No. 4,798,721 describes a composition comprising a latex particle. U.S. Patent Application No. 2005/0089490 A1 describes a composition comprising a water-dispersible styling polymer and a gel-forming polymer.

Although latex polymers have been used in some cosmetic products, there are special considerations for the use of latex in aerosol and non-aerosol spray products, namely that stability and firm-forming abilities must be maintained in a platform that is sprayable. There is thus a need for such a product.

SUMMARY OF THE DISCLOSURE

The instant disclosure relates to hair-styling compositions comprising a combination of soft and hard latex film-forming polymers. The ratio of the one or more soft latex film-forming polymers to the one or more hard latex film-forming polymers can vary but is typically about 1:1 to about 5:1 (one or more soft latex film-forming polymer:one or more hard latex film-forming polymer). This combination of latex film-forming polymers is typically included in high amounts of organic solvent, for example, at least 80 wt. % of organic solvent, based on the total weight of the hair styling composition. The shear viscosity of the resulting hair-styling compositions is up to about 70 cP at 23° C.

The soft latex film-forming polymers typically have a glass transition temperature (Tg) of less than 35° C.; and the hard latex film-forming polymers typically have a glass transition temperature (Tg) of 35° C. or more.

Non-limiting but useful examples of soft latex film-forming polymers include acrylate polymers and/or polyurethane polymers. In some cases, useful soft latex film-forming polymers are acrylate polymers derived from, for example, the homopolymerization or copolymerization of monomers chosen from (meth)acrylics, (meth)acrylates, (meth)acrylamides and/or vinyl homopolymers or copolymers. Useful polyurethane film-forming polymers include, for example, polyurethane-32, polyurethane-34, polyurethane-35, polyurethane-48, and a mixture thereof. Non-limiting but useful hard latex film-forming polymers include acrylate polymers, for example, polyacrylate-2 crosspolymer.

Coalescing agents and/or plasticizers can be used in the hair-styling compositions. Non-limiting examples of coalescing agents and/or plasticizers that may be used according to various embodiments include glycols and their derivatives, such as glycol ethers, for example, ethylene glycol, propylene glycol, diethylene glycol ethyl ether, diethylene glycol methyl ether, diethylene glycol butyl ether, diethylene glycol hexyl ether, diethylene glycol dibutyl ether, ethylene glycol methyl ether, ethylene glycol ethyl ether, ethylene glycol butyl ether, and ethylene glycol hexyl ether; glycol esters, such as diethylene glycol butyl ether acetate, propylene glycol dibenzoate and dipropylene glycol dibenzoate; cellulose esters, such as sucrose acetate; propylene glycol derivatives, such as propylene glycol phenyl ether, propylene glycol diacetate, dipropylene glycol butyl ether, tripropylene glycol butyl ether, propylene glycol methyl ether, dipropylene glycol ethyl ether, tripropylene glycol methyl ether and diethylene glycol methyl ether, propylene glycol butyl ether, and a mixture thereof.

The hair styling compositions of the instant disclosure typically include high amounts of organic solvent, for example, at least 80 wt. %, based on the total weight of the hair styling composition. Non-limiting examples of organic solvents include a C2 to C4 mono-alcohol, a volatile polyol, a volatile polyol ether, a volatile glycol ether, acetone, propylene carbonate, benzyl alcohol, and a mixtures thereof. In some cases, one or more organic solvents may be selected from the group consisting of ethanol, isopropyl alcohol, butanol, propylene glycol, butylene glycol, pentylene glycol, hexylene glycol, glycerol, isododecane, acetone, propylene carbonate, benzyl alcohol, and a mixture thereof.

The hair styling compositions are useable in a variety of hair styling products, for example, aerosol and non-aerosol hair sprays, hair mousses, hair gels, hair foams, hair gels, etc. In some cases, the hair styling compositions are included in non-aerosol hair styling products comprising a spray bottle, wherein the spray bottle contains a mechanical spray pump device and a hair styling composition of the instant disclosure. Additionally, the hair styling compositions can be included in aerosol hair styling products comprising a canister with a spraying device, wherein the canister contains propellant and a hair styling composition of the instant disclosure. Propellants for use in aerosol products are known and include, for example, dimethyl ether, propane, n-butane, isobutene, and a mixture thereof.

The hair styling compositions of the instant disclosure and the hair styling products containing the hair styling compositions are particularly useful in methods for styling hair. The hair styling compositions are typically applied to the hair (for example, by spraying). The hair may be shaped and/or styled before applying the hair styling compositions and the hair styling composition applied to hold or preserve the shape and style of the hair. Alternatively, the hair styling composition may be applied to the hair before shaping and/or styling the hair. After application (typically shortly after application before the compositions has completely dried) the hair is manipulated, shaped, and/or styled.

DETAILED DESCRIPTION OF THE DISCLOSURE

The hair styling compositions of the instant disclosure include a combination of hard and soft latex film-forming polymers, 15 wt. % of less of water; and at least 80 wt. % of organic solvent. One or more coalescing agents and/or plasticizers may also be included. The hair styling compositions are stable, provide long-lasting style control, and have a natural look and feel. In particular, the hair styling compositions allow for natural movement of the hair while retaining the desired shape and style of the hair, even under high humidity conditions.

There are several problems with providing a latex composition which is suitable for use as a hairspray. For example, many hairspray compositions utilize relatively high amounts of organic solvents (e.g., ethanol), but many latex polymers are unstable in such organic solvents. However, the latexes identified in the compositions described herein are selected for their stability in organic solvents.

Generally, latex film-forming polymers give poor films due to the fast evaporation of such solvents that prevent latex particles from coalescing. Without good film formation, desired properties (e.g., durable curl retention in hair) are unattainable. The inventors found that combinations of hard and soft latex film forming polymers in a sufficient amount of organic solvent (e.g., at least 80 wt. %) provide surprisingly good films that are useful for styling hair. The soft latex acts as a coalescent, thereby allowing film formation to occur. Other coalescing agents and/or plasticizers can be used to further improve the quality of the films and the curl retention of hair treated with the films. Without wishing to be bound by any particular theory, it is believed that the combination of hard and soft latex polymers swells in the organic solvent (such swelling can be seen by dynamic light scattering size measurements), thereby allowing the coalescing agents and/or plasticizers to penetrate into the swollen latex polymers to improve the quality and durability of the films.

Additionally, the above problems must be addressed but still maintain properties to be suitable as a spray. The amount of actives in cosmetic formulations must be high enough to be effective, but this often results in compositions with high viscosities. However, sprayable compositions must be thin enough to pass through the spray mechanism. Again, the selection of latexes allows for viscosities which are appropriate for spray applications.

The cosmetic compositions described herein may simultaneously address these problems. Accordingly, the hair styling compositions of the instant disclosure typically include:

one or more soft latex film-forming polymers having a glass transition temperature (Tg) of less than 35° C.;

one or more hard latex film-forming polymers having a glass transition temperature (Tg) of 35° C. or more;
less than 15 wt. % of water; and
at least 80 wt. % of one or more organic solvents;
wherein the composition has a shear viscosity of up to about 70 cP at 23° C.

The shear viscosity of the hair-styling compositions may be about 1, 2, 5, 10, 15, 20, 25, 30, 35, 40 cP to about 20, 25, 30, 35, 40, 45, 50, 55, 60 or 70 cP at 23° C. In some embodiments, the viscosity of the hair styling compositions may be about 10 cP to about 70 cP, about 15 cP to about 70 cP, or about 20 cP to about 70 cP at 23° C. The shear viscosity may be determined, for example, using an AGR-2 Rheometer from TA Instruments using a standard 20 mm 2° steel cone at 10,000 s$^{-1}$.

The ratio of the one or more soft latex film-forming polymers to the one or more hard film-forming polymers can vary but is typically about 1:10 to about 10:1. In some cases, the ratio is about 1:5 to about 5:1, about 1:3 to about 3:1, about 2:1 to about 1:2, about 1:1 to about 10:1, about 1:1 to about 5:1, about 1:1 to about 3:1, about 1.5:1 to about 4:1, about 1.5:1 to about 3:1, about 2:1 to about 4:1, or about 2:1 to about 3:1.

The soft latex film-forming polymers typically have a Tg of less than 35° C., for example, a Tg of about −90° C. to less than 35° C. The hard latex film-forming polymers typically have a Tg of 35° C. of more, for example a Tg of 35° C. to about 200° C.

Furthermore, a high Young's Modulus demonstrates a hard film, while a lower Young's Modulus represents a more elastic film. A high Strain demonstrates a stretchy, elastic film, while a lower Strain represents a more brittle film. The soft latex film-forming polymer may have a Young's modulus of about 0.1 MPa to about 10 MPa, and a strain, under stress at 0.5 MPa, of at least about 1%. Furthermore, the hard latex film-forming polymer may have a Young's modulus ranging from about 10 MPa to about 6 GPa, and a strain, under stress at 0.5 MPa, of less than about 5%.

In some cases, there is at least a 5° C. difference between the Tg of at least one soft latex film-forming polymer and at least one hard latex film-forming polymer included in the hair styling composition. Likewise, the difference between the Tg of the at least one soft latex film-forming polymer and the at least one hard latex film-forming polymer is at least 10° C., 15° C., 20° C., 25° C., 30° C., 35° C., 40° C., 45° C., or 50° C.

Non-limiting examples of soft latex film forming polymers having a Tg of less than 35° C. include acrylic/acrylate copolymer, acrylate/ethylhexyl acrylate copolymer, acrylates/ethylhexyl acrylate copolymer, acrylate copolymer, acrylic copolymer, polyurethane-2 (and) polymethyl methacrylate, polyurethane-32, polyurethane-34, polyurethane-35, and polyurethane-48.

In some cases, the one or more soft latex film-forming polymers include one or more acrylate polymers and/or polyurethane polymers. Non-limiting examples of polyurethane polymers include polyurethane-32, polyurethane-34, polyurethane-35, polyurethane-48, and a mixture thereof. The one or more acrylate polymers may be derived from the homopolymerization or copolymerization of monomers chosen from (meth)acrylics, (meth)acrylates, (meth)acrylamides and/or vinyl homopolymers or copolymers.

The total amount of the one or more soft latex film-forming polymers can vary but is typically about 1 to about 15 wt. %, based on the total weight of the hair styling composition. In some cases, the total amount of the one or more soft latex film-forming polymers is about 1 to about 12 wt. %, about 1 to about 10 wt. %, about 1 to about 8 wt. %, about 1 to about 6 wt. %, about 2 to about 15 wt. %, about 2 to about 12 wt. %, about 2 to about 10 wt. %, about 2 to about 8 wt. %, or about 2 to about 4 wt. %.

Non-limiting examples of hard latex film forming polymers having a Tg of 35° C. or more include acrylates copolymer, acrylates/hydroxyesters acrylate copolymer, polyacrylate-2 crosspolymer, acrylates/C1-2 succinates/hydroxyacrylates copolymer, acrylic copolymer, acrylates/hydroxyesters acrylate copolymer, ammonium acrylates copolymer, styrene/acrylates copolymer, copolymer of methyl methacrylate butyl acrylate and methacrylic acid, styrene/acrylates/ammonium methacrylate copolymer, alkyl acrylate/styrene copolymer, acrylate/VA copolymer, polycarbamyl polyglycol ester and PVP/polycarbamyl polyglycol ester. In some cases, the one or more hard latex film-forming polymers include an acrylate crosspolymer, for example, polyacrylate-2 crosspolymer.

The total amount of the one or more hard latex film-forming polymers can vary but is typically about 0.5 to about 15 wt. %, based on the total weight of the hair styling composition. In some cases, the total amount of the one or more hard latex film-forming polymers is about 0.5 to about 12 wt. %, about 0.5 to about 10 wt. %, about 0.5 to about 8 wt. %, about 0.5 to about 6 wt. %, about 0.5 to about 4 wt. %, about 1 to about 15 wt. %, about 1 to about 12 wt. %, about 1 to about 10 wt. %, about 1 to about 8 wt. %, about 1 to about 6 wt. %, about 1 to about 4 wt. %, or about 1 to about 3 wt. %.

Many cosmetically acceptable organic solvents are known and useable in the hair styling compositions of the instant disclosure. Non-limiting examples of organic solvents include a C2 to C4 mono-alcohol, benzyl alcohol, methanol, ethanol, propanol, butanol, a polyol, a polyol ether, a glycol ether, alkanes, cycloalkanes, alkyl ethers, petroleum ethers, ketones, methylene chloride, ethyl acetate, xylene, tolueneacetone, propylene carbonate, benzyl alcohol, ethanol, isopropyl alcohol, butanol, propylene glycol, butylene glycol, pentylene glycol, hexylene glycol, glycerol, isododecane, acetone, propylene carbonateisopropanol, acetone, dimethoxymethane and the mixture thereof.

The total amount of the one or more organic solvents may vary but is typically at least 80 wt. %, based on the total weight of the hair styling composition. For example, the total amount of the one or more organic solvents may be at least 80 wt. % to about 95 wt. %. In some instances, the total amount of the one or more organic solvents is higher than 80 wt. %, for example, at least 82 wt. %, at least 85 wt. %, at least 86 wt. %, at least 88 wt. %, at least 90 wt. %, up to about 95 wt. %. Furthermore, the total amount of the one or more organic solvents may be at least 80 wt. % to about 90 wt. %.

One or more coalescing agents and/or plasticizers are often useful in the hair styling compositions of the instant disclosure. Without wishing to be bound by theory, it is believed that the addition of coalescing agents and/or plasticizers may lower the glass transition temperature (Tg), decrease the Young's modulus, and increase the strain of latex polymers and/or the films formed by latex polymers. Further, the at least one coalescing agent and/or plasticizer may also be used to aid coating formation of the latex film to form a continuous and homogeneous film or coating and to improve adhesion. While the lowering of the Tg of the latex polymers can result in a softening of the film or coating formed by the latex polymers, it has been found that the coating or film produced on hair treated with the compositions of the disclosure surprisingly and unexpectedly imparts a strong styling hold to the hair while leaving the hair with a natural/clean feel and look. As such, the flexibility and stiffness of the resulting film or coating may be more balanced, and thus impart a better style and stronger hold to hair.

Non-limiting examples of coalescing agents and/or plasticizers that may be used according to various embodiments include glycols and their derivatives, such as glycol ethers, for example, diethylene glycol ethyl ether, diethylene glycol methyl ether, diethylene glycol butyl ether, diethylene glycol hexyl ether, diethylene glycol dibutyl ether, ethylene glycol methyl ether, ethylene glycol ethyl ether, ethylene glycol butyl ether, and ethylene glycol hexyl ether; glycol esters, such as diethylene glycol butyl ether acetate, propylene glycol dibenzoate and dipropylene glycol dibenzoate; cellulose esters, such as sucrose acetate; propylene glycol derivatives, such as propylene glycol phenyl ether, propylene glycol diacetate, dipropylene glycol butyl ether, tripropylene glycol butyl ether, propylene glycol methyl ether, dipropylene glycol ethyl ether, tripropylene glycol methyl ether and diethylene glycol methyl ether, propylene glycol butyl ether, and a mixture thereof.

In some cases, acid esters, for example carboxylic acid esters, are useful coalescing agents and/or plasticizers. Non-limiting examples include acetates, such as glycerol triacetate; citrates, such as triethyl citrate, tributyl citrate, triethyl acetylcitrate, tributyl acetylcitrate and tri(2-ethylhexyl)acetylcitrate; phthalates, such as diethyl phthalate, dibutyl phthalate, dioctyl phthalate, dipentyl phthalate, dimethoxyethyl phthalate, butyl phthalate, and 2-ethylhexyl phthalate; phosphates, such as tricresyl phosphate, tributyl phosphate, triphenyl phosphate and tributoxyethyl phosphate; tartrates, such as dibutyl tartrate; and sebacates, such as dimethyl sebacate, dibutyl sebacate, and a mixture thereof.

Additionally, in some cases, the fatty acid esters, such as adipic acid esters, are useful coalescing agents and/or plasticizers. Non-limiting examples include diisobutyl adipate and diethyl adipate. Stearic acid esters, such as ethyl stearate, and palmitic acid esters, such as 2-ethylhexyl palmitate, succinates, abietates, caprylates, caproates, enanthates, and myristates may also be used. In some cases, the one or more coalescing agents and/or plasticizers may include carbonates, such as ethylene carbonate and propylene carbonate; benzyl benzoate, sucrose benzoate, butyl acetylricinoleate, glyceryl acetylricinoleate, butyl glycolate, camphor, N-ethyl-o,p-toluenesulphonamide, ethyl tosylamide, and a mixture thereof.

Furthermore, in some cases oxyethylenated derivatives, such as oxyethylenated oils, may be useful coalescing agents and/or plasticizers. Non-limiting examples include vegetable oil, castor oil, oils of natural origin, including non-drying oils and those comprising at least one fatty acid chosen from caprylic acid, capric acid, lauric acid, myristic acid, palmitic acid, stearic acid, oleic acid, ricinoleic acid, linoleic acid, linolenic acid, arachidic acid, gadoleic acid, behenic acid, erucic acid, brassidic acid, cetoleic acid, lignoceric acid and nervonic acid. In at least certain exemplary embodiments, the oils are chosen from triglycerides composed of esters of fatty acids and of glycerol, of which the fatty acids have varied chain lengths from C4 to C24 that can be linear or branched and saturated or unsaturated. Non-limiting examples of oils include heptanoic or octanoic triglycerides, groundnut, babassu, coconut, grape seed, cottonseed, maize, maize germ, mustard seed, palm, rapeseed, sesame, soybean, sunflower, wheat germ, canola, apricot, mango, castor, shea, avocado, olive, sweet almond, almond, peach, walnut, hazelnut, macadamia, jojoba, alfalfa, poppy, pumpkinseed, cucumber, blackcurrant, evening primrose, millet, barley, guinea, rye, safflower, candlenut, passionflower, musk rose or shea butter oils or triglycerides of caprylic/capric acids, and a mixture thereof.

The total amount of the one or more coalescing agents and/or plasticizers may vary but is typically about 0.01 to about 10 wt. %, based on the total weight of the hair styling composition. In some cases, the total amount of the one or more coalescing agents and/or plasticizers is about 0.01 to about 8 wt. %, about 0.01 to about 6 wt. %, about 0.01 to about 5 wt. %, about 0.01 to about 3 wt. %, about 0.01 to about 2 wt. %, or about 0.01 to about 1 wt. %. Additionally, the total amount of the one or more coalescing agents and/or plasticizers may be about 0.1 to about 10 wt. %, about 0.1 to about 8 wt. %, about 0.1 to about 6 wt. %, about 0.1 to about 5 wt. %, about 0.1 to about 3 wt. %, about 0.1 to about 2 wt. %, or about 0.1 to about 1 wt. %.

In certain embodiments, the hair styling compositions of the instant disclosure include:
- about 1 to about 10 wt. %, about 1 to about 8 wt. %, or about 1 to about 6 wt. % of one or more soft latex film-forming polymers having a glass transition temperature (Tg) of less than 35° C., for example, acrylates copolymer;
- about 0.1 to about 6 wt. %, about 0.5 to about 5 wt. %, or about 0.5 to about 4 wt. % of one or more hard latex film-forming polymers having a glass transition temperature (Tg) of 35° C. or more, for example, polyacrylate-2 crosspolymer;
- about 0.01 to about 5 wt. %, about 0.1 to about 5 wt. %, or about 0.1 to about 3 wt. % of one or more coalescing agents and/or plasticizers, for example, carboxylic acid esters such as acetates, citrates, phthalates, phosphates, tartrates, sebacates, and a mixture thereof.
- about 0.1 to about 15 wt. %, about 1 to about 15 wt. %, or about 5 to about 15 wt. % of water; and
- at least 80 wt. % one or more volatile organic solvents such as methanol, ethanol, propanol, isopropanol, butanol, acetone, dimethoxymethane, dimethyl ether, or a mixture thereof, and in particular ethanol.

The hair styling composition may have a shear viscosity of up to about 70 cP at 23° C. However, the shear viscosity may be about 10 cP to about 70 cP, about 15 cP to about 70 cP, or about 20 cP to about 70 cP at 23° C.

The ratio of the one or more soft latex film-forming polymers to the one or more hard film-forming polymers can vary but is typically about 1:10 to about 10:1. In some cases, the ratio is about 1:5 to about 5:1, about 1:3 to about 3:1, about 2:1 to about 1:2, about 1:1 to about 10:1, about 1:1 to about 5:1, about 1:1 to about 3:1, about 1.5:1 to about 4:1, about 1.5:1 to about 3:1, about 2:1 to about 4:1, or about 2:1 to about 3:1.

In some instances, the one or more coalescing agents and/or plasticizers include one or more citrates, for example one or more citrates selected from the group consisting of triethyl citrate, tributyl citrate, triethyl acetylcitrate, tributyl acetylcitrate, tri(2-ethylhexyl)acetylcitrate, and a mixture thereof.

In some embodiments, the hair styling compositions of the instant disclosure include
- about 1 to about 10 wt. %, about 1 to about 8 wt. %, or about 1 to about 6 wt. % of one or more soft latex film-forming polymers having a glass transition temperature (Tg) of less than 35° C., for example, one or more polyurethane polymers selected from the group consisting of polyurethane-32, polyurethane-34, polyurethane-35, polyurethane-48, and a mixture thereof;
- about 0.1 to about 6 wt. %, about 0.5 to about 5 wt. %, or about 0.5 to about 4 wt. % of one or more hard latex film-forming polymers having a glass transition temperature (Tg) of 35° C. or more, for example, polyacrylate-2 crosspolymer;
- about 0.01 to about 5 wt. %, about 0.1 to about 5 wt. %, or about 0.1 to about 3 wt. % of one or more coalescing agents and/or plasticizers, for example, carboxylic acid esters such as acetates, citrates, phthalates, phosphates, tartrates, sebacates, and a mixture thereof.
- about 0.1 to about 15 wt. %, about 1 to about 15 wt. %, or about 5 to about 15 wt. % of water; and
- at least 80 wt. % one or more volatile organic solvents such as methanol, ethanol, propanol, isopropanol, butanol, acetone, dimethoxymethane, dimethyl ether, or a mixture thereof, and in particular ethanol.

The hair styling composition may have a shear viscosity of up to about 70 cP at 23° C. However, the shear viscosity may be about 10 cP to about 70 cP, about 15 cP to about 70 cP, or about 20 cP to about 70 cP at 23° C.

The ratio of the one or more soft latex film-forming polymers to the one or more hard film-forming polymers can vary but is typically about 1:10 to about 10:1. In some cases, the ratio is about 1:5 to about 5:1, about 1:3 to about 3:1, about 2:1 to about 1:2, about 1:1 to about 10:1, about 1:1 to about 5:1, about 1:1 to about 3:1, about 1.5:1 to about 4:1, about 1.5:1 to about 3:1, about 2:1 to about 4:1, or about 2:1 to about 3:1.

In some instances, the one or more coalescing agents and/or plasticizers include one or more citrates, for example one or more citrates selected from the group consisting of triethyl citrate, tributyl citrate, triethyl acetylcitrate, tributyl acetylcitrate, tri(2-ethylhexyl)acetylcitrate, and a mixture thereof.

The instant disclosure further relates to hair styling products that include and/or incorporate the hair styling compositions of the instant disclosure. Such products include, for example, non-aerosol and aerosol hair spray products, pump hair spray products, hair mousse products, hair foam products, hair gel products, etc. The hair styling products may use air/propellant to expel and apply the hair styling compositions to the hair of a user or may incorporate air/propellant into the compositions to provide a certain form for the products (e.g., a foam, gel, mousse, etc.).

In some cases, the instant disclosure relates to a non-aerosol hair styling product comprising a spray bottle, the spray bottle containing a mechanical spray pump device and a hair styling composition as disclosed herein. When the hair treatment product of the present disclosure is provided in the form of a sprayable non-aerosol hair spray product, the hair styling composition may be sprayed by means of a suitable, mechanical spraying device. Spray devices of the mechanical type are devices which allow the spraying of a composition without using a propellant. Suitable mechanical spray devices are, e.g., spray pumps or elastic containers provided with a spray valve, into which the cosmetic composition in accordance with present invention is filled under pressure, whereby the elastic container is expanded and wherein the cosmetic composition is continuously discharged if the valve is open, due to the contraction of the elastic container.

Alternatively, in some cases, the instant disclosure relates to an aerosol hair styling product comprising a container or canister, the container or canister containing propellant and a hair styling composition as disclosed herein, and usually having a spray button or other type of dispensing device. Propellants are known and various types may be used in the instant products. Non-limiting examples of propellants include dimethyl ether, lower alkanes, such as n-butane, isobutene and propane, fluorohydrocarbons, such as F 152a (1,1-difluorethane) or F 134 (tetrafluorethane), as well as propellants which are present at the pressures in question in gaseous forms such as $N_2$, $N_2O$ and $CO_2$ as well as mixtures of the above-mentioned propellants. In some cases, particularly useful propellants include dimethyl ether, hydrofluorocarbon 152A, isobutane, propane, butane, and a mixture thereof.

Various aerosol devices may be employed. Typically, an aerosol device includes a vessel (e.g., a container or canister) and a dispensing device for dispensing the content of the container, such as a spray device. Contained inside the vessel is a vapor phase comprising propellant(s) and a juice phase (liquid phase) comprising a hair styling composition. The role of the vapor phase (the propellant(s) in particular) is to provide pressure for expelling the juice phase from the vessel. For example, typical aerosol hair spray devices expel the juice phase in the form of a mist of dispersed droplets. The juice phase is primarily comprised of the hair styling compositions of the instant disclosure. Small amounts of propellant(s) or other materials from the vapor phase may be present in the juice phase, for example, to the extent that these components may be partially dispersed or solubilized in the juice phase. Likewise, the vapor phase is primarily comprised of propellant(s). Small amounts of juice phase (or components of the juice phase) may be present in the vapor phase to the extent that the juice phase (or components of the juice phase) are dispersed or solubilized in the vapor phase.

The total amount of propellant incorporated into an aerosol product such as an aerosol hair spray product may vary. In some cases, however, an aerosol hair spray product may include about 10 to about 95 wt. % of propellant, based on the total weight of the hair styling compositions and propellant (i.e., the total weight of the content inside of a container or canister that houses the hair styling composition and propellant). In some cases, the total amount of propellant may be about 20 to about 90 wt. %, about 30 to about 90 wt. %, about 40 to about 90 wt. %, about 50 to about 90 wt. %, or about 60 to about 90 wt. %.

When the hair styling product in accordance with present disclosure is provided in the form of a hair foam (mousse) product, the product comprises at least one conventional foaming agent known in the art for this purpose. The composition is foamed with or without the aid of propellants or chemical propellants. A product in accordance with present disclosure comprises as additional component a device for the provision of a foam of the composition. Devices for providing a foam are devices which allow the provision of a foam starting from a liquid, with or without the use of a propellant. Suitable mechanical foaming devices are, e.g., usual foam pumps, or usual aerosol foaming heads.

When the hair styling product in accordance with present disclosure is provided in the form of a hair gel product, it may include at least one gel forming substance in an amount of 0.05 to 10 wt. %, or about 0.1 to 2 weight %, based on the total weight of the hair styling gel. The viscosity of the gel may be from about 100 bis 50,000 mm²/s, or about 1,000 bis 15,000 mm²/s at 25° C., measured as dynamic viscosity using a Bohlin Rheometer CS, measurement body C25 using a shear velocity of 50 s⁻¹.

In some embodiments, the instant disclosure relates to an aerosol hair spray product comprising a canister or container, the canister or container containing:
(i) a vapor phase comprising a propellant; and
(ii) a juice phase comprising a hair styling composition comprising:

about 1 to about 10 wt. %, about 1 to about 8 wt. %, or about 1 to about 6 wt. % of one or more soft latex film-forming polymers having a glass transition temperature (Tg) of less than 35° C., for example, acrylates copolymer;

about 0.1 to about 6 wt. %, about 0.5 to about 5 wt. %, or about 0.5 to about 4 wt. % of one or more hard latex film-forming polymers having a glass transition temperature (Tg) of 35° C. or more, for example, polyacrylate-2 crosspolymer;

about 0.01 to about 5 wt. %, about 0.1 to about 5 wt. %, or about 0.1 to about 3 wt. % of one or more coalescing agents and/or plasticizers, for example, carboxylic acid esters such as acetates, citrates, phthalates, phosphates, tartrates, sebacates, and a mixture thereof.

about 0.1 to about 15 wt. %, about 1 to about 15 wt. %, or about 5 to about 15 wt. % of water; and at least 80 wt. % one or more volatile organic solvents such as methanol, ethanol, propanol, isopropanol, butanol, acetone, dimethoxymethane, dimethyl ether, or a mixture thereof, and in particular ethanol;

wherein the weight percentages provided above relate to the total weight of the hair styling compositions without propellant.

The hair styling composition may have a shear viscosity of up to about 70 cP at 23° C. However, the shear viscosity may be about 10 cP to about 70 cP, about 15 cP to about 70 cP, or about 20 cP to about 70 cP at 23° C.

The ratio of the one or more soft latex film-forming polymers to the one or more hard film-forming polymers can vary but is typically about 1:10 to about 10:1. In some cases, the ratio is about 1:5 to about 5:1, about 1:3 to about 3:1, about 2:1 to about 1:2, about 1:1 to about 10:1, about 1:1 to about 5:1, about 1:1 to about 3:1, about 1.5:1 to about 4:1, about 1.5:1 to about 3:1, about 2:1 to about 4:1, or about 2:1 to about 3:1.

In some instances, the one or more coalescing agents and/or plasticizers include one or more citrates, for example one or more citrates selected from the group consisting of triethyl citrate, tributyl citrate, triethyl acetylcitrate, tributyl acetylcitrate, tri(2-ethylhexyl)acetylcitrate, and a mixture thereof.

In some embodiments, the instant disclosure relates to an aerosol hair spray product comprising a canister or container, the canister or container containing:
(i) a vapor phase comprising a propellant; and
(ii) a juice phase comprising a hair styling composition comprising:

about 1 to about 10 wt. %, about 1 to about 8 wt. %, or about 1 to about 6 wt. % of one or more soft latex film-forming polymers having a glass transition temperature (Tg) of less than 35° C., for example, one or more polyurethane polymers selected from the group consisting of polyurethane-32, polyurethane-34, polyurethane-35, polyurethane-48, and a mixture thereof;

about 0.1 to about 6 wt. %, about 0.5 to about 5 wt. %, or about 0.5 to about 4 wt. % of one or more hard latex film-forming polymers having a glass transition temperature (Tg) of 35° C. or more, for example, polyacrylate-2 crosspolymer;

about 0.01 to about 5 wt. %, about 0.1 to about 5 wt. %, or about 0.1 to about 3 wt. % of one or more coalescing agents and/or plasticizers, for example, carboxylic acid esters such as acetates, citrates, phthalates, phosphates, tartrates, sebacates, and a mixture thereof.

about 0.1 to about 15 wt. %, about 1 to about 15 wt. %, or about 5 to about 15 wt. % of water; and at least 80 wt. % one or more volatile organic solvents such as methanol, ethanol, propanol, isopropanol, butanol, acetone, dimethoxymethane, dimethyl ether, or a mixture thereof, and in particular ethanol;
wherein the weight percentages provided above relate to the total weight of the hair styling compositions without propellant.

The hair styling composition may have a shear viscosity of up to about 70 cP at 23° C. However, the shear viscosity may be about 10 cP to about 70 cP, about 15 cP to about 70 cP, or about 20 cP to about 70 cP at 23° C.

The ratio of the one or more soft latex film-forming polymers to the one or more hard film-forming polymers can vary but is typically about 1:10 to about 10:1. In some cases, the ratio is about 1:5 to about 5:1, about 1:3 to about 3:1, about 2:1 to about 1:2, about 1:1 to about 10:1, about 1:1 to about 5:1, about 1:1 to about 3:1, about 1.5:1 to about 4:1, about 1.5:1 to about 3:1, about 2:1 to about 4:1, or about 2:1 to about 3:1.

In some instances, the one or more coalescing agents and/or plasticizers include one or more citrates, for example one or more citrates selected from the group consisting of triethyl citrate, tributyl citrate, triethyl acetylcitrate, tributyl acetylcitrate, tri(2-ethylhexyl)acetylcitrate, and a mixture thereof.

The instant disclosure further relates to styling the hair are disclosed. Such methods include, for example, applying a hair styling compositions according to the disclosure to the hair. Additionally, the methods may include shaping, reshaping, positioning, repositioning, adding volume to, curling, or straightening the hair, in order to achieve a certain hair style or appearance. The hair styling composition may be applied by spraying, for example, especially when the hair styling composition is used in a hair spray product. In instances where the hair styling product is a mousse, a foam, or gel, the product may be applied directly to the hair or may be applied to the hand or a styling device that subsequently applies the product to the hair for styling. Furthermore, the hair styling compositions may be applied before styling the hair or may be applied after styling the hair. If applied before styling the hair, the hair styling composition may be applied to the hair and the hair may subsequently be styled with styling devices and/or treatments such as a blow drying, a heat iron (curling iron, straightening iron, etc.), combing, etc.

More exhaustive but non-limiting latex film-forming polymers that are useful in the hair styling compositions of the instant disclosure are provided below. Whether the latex film-forming polymers are characterized as "hard" or "soft" can be determined based on the polymer's Tg, for example, using a TA Universal Analysis 2000 from TA Instruments with software for automation. Dried latex film Samples (5-10 mg) are heated under dry nitrogen gas to about 200° C. at a heating rate of about 10° C./min and cooled to about −80° C. at a rate of about 10° C./min with a two-cycle minimum. Tg is defined as the midpoint of the curve.

As used herein, a film-forming polymer is meant to include a polymer that is capable, by itself or in the presence of an auxiliary film-forming agent, of forming a macroscopically continuous film that adheres to keratin materials, and preferably a cohesive film, better still, a film whose cohesion and mechanical properties are such that said film can be isolated and manipulated individually, for example, when said film is prepared by pouring onto a non-stick surface such as Teflon-coated or silicone-coated surface. In addition, as used herein, a non-film-forming polymer is meant to include a polymer which will not form a film at ambient temperature or below, or in other words, will only form a film at temperatures above ambient. For purposes of this disclosure, ambient temperature is taken as being below 40° C. such as in the range of 15° C. to 30° C.

The latex film-forming polymers may being the form of aqueous dispersions prior to formulating the compositions of the disclosure. The aqueous dispersions may be obtained through an emulsion polymerization of monomers wherein the resulting latex polymers have a particle size lower than about 1 μm. In some cases, a dispersion prepared by the polymerization in water of one or more monomers having a polymerizable double bond may be chosen. In another exemplary embodiment, the aqueous dispersions obtained through an emulsion polymerization may be spray-dried.

In other embodiments, the latex polymers are produced from condensation reactions between monomers and subsequently dispersed in an aqueous medium.

As noted above, the latex film-forming polymers often exist as dispersed polymer particles in a dispersion medium, such as an aqueous dispersion medium. The latex polymers may, in certain embodiments, each be dispersed in independent dispersion media. In yet further embodiments, the latex polymers may be dispersed together in the same dispersion medium.

The dispersion medium typically comprises at least one solvent, for example, a solvent such as water. The dispersion medium may further comprise at least one solvent chosen from cosmetically acceptable organic solvents. Cosmetically acceptable organic solvents may, in various embodiments, be water-miscible, e.g. capable of forming at 25° C. a homogeneous mixture that is transparent, or substantially transparent, to the eye. For instance, cosmetically acceptable organic solvents may be chosen from lower monoalcohols, such as those containing from about 1 to 5 carbon atoms, for example ethanol and isopropanol; polyols, including glycols, such as those containing from about 2 to 8 carbon atoms, for example propylene glycol, ethylene glycol, 1,3-butylene glycol, dipropylene glycol, hexylene glycol, and glycerin; hydrocarbons, such as, for example, isododecane and mineral oil; and silicones, such as dimethicones, cyclomethicones, and cyclopentasiloxane; as well as mixtures thereof.

In at least one embodiment, the solvent of the dispersion is water. In other embodiments, the solvent of the dispersion medium is water and at least one cosmetically acceptable organic solvent. In further embodiments, the solvent comprises water. In yet further embodiments, the solvent of the dispersion medium primarily comprises water. For example, the solvent of the dispersion medium may, in at least certain exemplary embodiments, comprise greater than 50% water, such as greater than 55% water, greater than 60% water, greater than 65% water, greater than 70% water, greater than 75% water, greater than 80% water, greater than 85% water, greater than 90% water, greater than 95% water, greater than 96% water, greater than 97% water, greater than 98% water, or greater than 99% water.

In embodiments according to the disclosure, the latex polymer particles may not be soluble in the solvent of the dispersion medium, i.e. are not water soluble and/or are not soluble in the at least one cosmetically acceptable organic solvent. Accordingly, the latex polymers retain their particulate form in the solvent or solvents chosen. In at least certain exemplary embodiments, latex particles according to the disclosure may have an average diameter ranging up to about 1000 nm, such as from about 50 nm to about 800 nm, or from about 100 nm to about 500 nm. Such particle sizes may be measured with a laser granulometer (e.g. Brookhaven B190).

In various embodiments, the latex polymers may, independently, be neutralized, partially neutralized, or unneutralized. In exemplary embodiments where the latex polymers are neutralized or partially neutralized, the particle size may be, for example, greater than about 800 nm. In at least certain embodiments, the particulate form of the latex polymers is retained in the dispersion medium.

In further embodiments, the latex polymers may be chosen from uncharged and charged latex polymers. Thus, the latex polymers may, according to various exemplary embodiments, be chosen from nonionic latex polymers, cationic latex polymers, and anionic latex polymers.

As non-limiting examples of latex polymers that may be used, mention may be made, independently, of acrylate latex polymers and polyurethane latex polymers. By way of non-limiting example only, the latex film-forming polymers may be chosen from acrylate latex polymers, such as those resulting from the homopolymerization or copolymerization of monomers chosen from (meth)acrylics, (meth)acrylates, (meth)acrylamides and/or vinyl homopolymers or copolymers. The term "(meth)acryl" and variations thereof, as used herein, means acryl or methacryl. The (meth)acrylic monomers may be chosen from, for example, acrylic acid, methacrylic acid, citraconic acid, itaconic acid, maleic acid, fumaric acid, crotonic acid, and maleic anhydride. Additional non-limiting examples of (meth)acrylic monomers include C1-C8 alkyl (meth)acrylic, such as, for example, methyl (meth)acrylic, ethyl (meth)acrylic, propyl (meth)acrylic, isopropyl (meth)acrylic, butyl (meth)acrylic, tert-butyl (meth)acrylic, pentyl(meth) acrylic, isopentyl (meth)acrylic, neopentyl (meth)acrylic, hexyl (meth)acrylic, isohexyl (meth)acrylic, 2-ethylhexyl (meth)acrylic, cyclohexyl (meth)acrylic, isohexyl (meth)acrylic, heptyl (meth)acrylic, isoheptyl (meth)acrylic, octyl (meth)acrylic, isooctyl (meth)acrylic, as well as combinations of any of the above.

The esters of (meth)acrylic monomers may be, by way of non-limiting example, C1-C8 alkyl (meth)acrylates such as methyl (meth)acrylate, ethyl (meth)acrylate, propyl (meth)acrylate, isopropyl (meth)acrylate, butyl (meth)acrylate, tert-butyl (meth)acrylate, pentyl(meth) acrylate, isopentyl (meth)acrylate, neopentyl (meth)acrylate, hexyl (meth)acrylate, isohexyl (meth)acrylate, 2-ethylhexyl (meth)acrylate, cyclohexyl (meth)acrylate, isohexyl (meth)acrylate, heptyl (meth)acrylate, isoheptyl (meth)acrylate, octyl (meth)acrylate, isooctyl (meth)acrylate, allyl (meth)acrylate, and combinations thereof. Additional and non-limiting examples include C1-C8 alkoxy (meth)acrylates, such as methoxy (meth)acrylate, ethoxy (meth)acrylate, propyl oxide (meth)acrylate, isopropyl oxide (meth)acrylate, butyl oxide (meth)acrylate, tert-butyl oxide (meth)acrylate, pentyl oxide (meth) acrylate, isopentyl oxide (meth)acrylate, neopentyl oxide (meth)acrylate. The esters may be, by way of non-limiting example, C2-C6 hydroxy alkyl (meth)acrylates, such as hydroxy ethyl (meth)acrylate, 2-hydroxypropyl (meth)acrylate, glycidyl (meth)acrylate, ethylene glycol di(meth)acrylate, polyethylene glycol mono(meth)acrylate, 1,4-butane diol di(meth)acrylate, 1,6,hexane diol di(meth)acrylate, and any combination thereof. The esters may be, by way of non-limiting example, aryl (meth)acrylates such as benzyl (meth)acrylate, phenyl (meth)acrylate, and any combination thereof. The esters can further contain amino groups such as aminoethyl (meth)acrylate, N,N-dimethylaminoethyl (meth)acrylate, N,N-dimethylaminopropyl (meth)acrylate, N,N-dimethylaminodimethylpropyl (meth)acrylate, N,N-diethyleaminoethyl (meth)acrylate, and N,N,N-trimethylaminoethyl (meth)acrylate; and salts of the ethylenic amines. The alkyl group of the esters may be either fluorinated or perfluorinated, e.g. some or all of the hydrogen atoms of the alkyl group are substituted with fluorine atoms. The monomers can also be fluorine-containing monomers, such as, by way of non-limiting example, trifluoroethyl methacrylate, 2,2,3,3-tetrafluoropropyl methacrylate, 2,2,3,3,4,4-hexafluorobutyl methacrylate, perfluorooctyl methacrylate and perfluorooctyl acrylate; and silicone macromonomers.

The amides of (meth)acrylic monomers can, for example, be made of (meth)acrylamides, and especially N-alkyl (meth)acrylamides, in particular N—(C1-C12) alkyl (meth)acrylates such as N-ethyl (meth)acrylamide, N-t-butyl (meth)acrylamide, N-t-octyl (meth)acrylamide, N-methylol (meth)acrylamide and N-diacetone (meth)acrylamide, and any combination thereof.

The vinyl monomers can include, but are not limited to, vinyl cyanide compounds such as acrylonitrile and methacrylonitrile; vinyl esters such as vinyl formate, vinyl acetate, vinyl propionate, vinyl neodecanoate, vinyl pivalate, vinyl benzoate and vinyl t-butyl benzoate, triallyl cyanurate; vinyl halides such as vinyl chloride and vinylidene chloride; aromatic mono- or divinyl compounds such as styrene, α-methylstyrene, chlorostyrene, alkylstyrene, divinylbenzene and diallyl phthalate, and combination thereof. Other non-limiting ionic monomers can include para-styrensulfonic, vinylsulfonic, 2-(meth)acryloyloxyethylsulfonic, 2-(meth)acrylamido-2-methylpropylsulfonic acids. The list of monomers given is not limiting, and it should be understood that it is possible to use any monomer known to those skilled in the art which includes acrylic and/or vinyl monomers (including monomers modified with a silicone chain).

Silicone acrylic polymers may also optionally be used as vinyl polymer in at least one exemplary and non-limiting embodiment. In at least certain, non-limiting exemplary embodiments, acrylic latex polymers may be chosen from aqueous dispersions of Methacrylic Acid/Ethyl Acrylate copolymer (INCI: Acrylates Copolymer, such as LUVIFLEX® SOFT by BASF), PEG/PPG-23/6 Dimethicone Citraconate/C10-30 Alkyl PEG-25 Methacrylate/Acrylic Acid/Methacrylic Acid/Ethyl Acrylate/Trimethylolpropane PEG-15 Triacrylate copolymer (INCI: Polyacrylate-2 Crosspolymer, such as FIXATE SUPERHOLD™ by Lubrizol), Styrene/Acrylic copolymer (such as NEOCRYL® A-1120, DSM), Ethylhexyl Acrylate/Methyl Methacrylate/Butyl Acrylate/Acrylic Acid/Methacrylic Acid copolymer (INCI: Acrylates/Ethylhexyl Acrylate Copolymer, such as DAITOSOL 5000SJ, Daito Kasei Kogyo), Acrylic/Acrylates Copolymer (INCI name: Acrylates Copolymer, such as DAITOSOL 5000AD, Daito Kasei Kogyo), and Acrylic copolymers and Acrylates Copolymers, such as those known under the tradenames VINYSOL 2140 (Daido Chemical), ACULYN™ 33 (Dow Chemical), LUVIMER® MAE (BASF), or BALANCE CR (AKZO NOBEL).

In yet further exemplary and non-limiting embodiments, the latex film-forming polymers may be chosen from polyurethane latex polymers, such as aqueous polyurethane dispersions comprising the reaction products of (i), (ii), and/or (iii), defined below.

Reaction product (i) may be any prepolymer according to the formula:

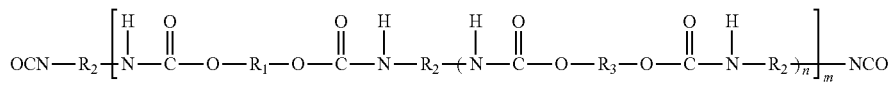

wherein R1 is chosen from bivalent radicals of a dihydroxyl functional compound, R2 is chosen from hydrocarbon radicals of an aliphatic or cycloaliphatic polyisocyanate, and R3 is chosen from radicals of a low molecular weight diol, optionally substituted with ionic groups, n ranges from about 0 to about 5, and m is greater than about 1.

Suitable dihydroxyl compounds for providing the bivalent radical R1 include those having at least two hydroxy groups, and having number average molecular weights ranging from about 700 to about 16,000, such as, for example, from about 750 to about 5000. Non-limiting examples of the high molecular weight compounds include polyester polyols, polyether polyols, polyhydroxy polycarbonates, polyhydroxy polyacetals, polyhydroxy polyacrylates, polyhydroxy polyester amides, polyhydroxy polyalkadienes and polyhydroxy polythioethers. In various embodiments, polyester polyols, polyether polyols, and polyhydroxy polycarbonates may be chosen. Mixtures of such compounds are also within the scope of the disclosure.

The polyester diol(s) may optionally be prepared from aliphatic, cycloaliphatic, or aromatic dicarboxylic or polycarboxylic acids, or anhydrides thereof; and dihydric alcohols such as diols chosen from aliphatic, alicyclic, or aromatic diols.

The aliphatic dicarboxylic or polycarboxylic acids may be chosen from, for example: succinic, fumaric, glutaric, 2,2-dimethylglutaric, adipic, itaconic, pimelic, suberic, azelaic, sebacic, maleic, malonic, 2,2-dimethylmalonic, nonanedicarboxylic, decanedicarboxylic, dodecanedioic, 1,3-cyclohexanedicarboxylic, 1,4-cyclohexane-dicarboxylic, 2,5-norboranedicarboxylic, diglycolic, thiodipropionic, 2,5-naphthalene-dicarboxylic, 2,6-naphthalenedicarboxylic, phthalic, terephthalic, isophthalic, oxanic, o-phthalic, tetrahydrophthalic, hexahydrophthalic or trimellitic acid.

The acid anhydrides may, in further exemplary embodiments, be chosen from o-phthalic, trimellitic or succinic acid anhydride or a mixture thereof. By way of non-limiting example only, the dicarboxylic acid may be adipic acid.

The dihydric alcohols may be chosen from, for example, ethanediol, ethylene glycol, diethylene glycol, triethylene glycol, trimethylene glycol, tetraethylene glycol, 1,2-propanediol, dipropylene glycol, tripropylene glycol, tetrapropylene glycol, 1,3-propanediol, 1,4-butanediol, 1,3-butanediol, 2,3-butanediol, 1,5-pentanediol, 1,6-hexanediol, 2,2-dimethyl-1,3-propanediol, 1,4-dihydroxycyclohexane, 1,4-dimethylolcyclohexane, cyclohexanedimethanol, 1,8-octanediol, 1,10-decanediol, 1,12-dodecanediol, neopentyl glycol, and mixtures thereof. The cycloaliphatic and/or aromatic dihydroxyl compounds may also be suitable as the dihydric alcohol(s) for the preparation of the polyester polyol(s).

The polyester diols may also be chosen from homopolymers or copolymers of lactones, which are, in at least certain embodiments, obtained by addition reactions of lactones or lactone mixtures, such as butyrolactone, ε-caprolactone and/or methyl-ε-caprolactone with the appropriate polyfunctional, e.g. difunctional, starter molecules such as, for example, the dihydric alcohols mentioned above. The corresponding polymers of ε-caprolactone may be chosen in at least some embodiments.

The polyester polyol, e.g. polyester diol, radical R1, may be obtained by polycondensation of dicarboxylic acids, such as adipic acid, with polyols, e.g. diols, such as hexanediol, neopentyl glycol, and mixtures thereof.

The polycarbonates containing hydroxyl groups comprise those known per se, such as the products obtained by reacting diols, such as (1,3)-propanediol, (1,4)-butanediol and/or (1,6)-hexanediol, diethylene glycol, triethylene glycol, or tetraethylene glycol with diaryl carbonates, for example diphenyl carbonate or phosgene.

Optional polyether polyols may be obtained in any known manner by reacting starting compounds which contain reactive hydrogen atoms with alkylene oxides, such as, for example, ethylene oxide; propylene oxide; butylene oxide; styrene oxide; tetrahydrofuran; or epichlorohydrin, or with mixtures of these alkylene oxides. In at least certain embodiments, the polyethers do not contain more than about 10% by weight of ethylene oxide units. For example, polyethers obtained without addition of ethylene oxide may be chosen.

Polyethers modified with vinyl polymers are also suitable according to various embodiments of the disclosure. Products of this type can be obtained by polymerization, for example, of styrene and acrylonitrile in the presence of polyethers, for example as described in U.S. Pat. Nos. 3,383,351; 3,304,273; 3,523,095; 3,110,695; and German patent 1 152 536.

Among the polythioethers which may be chosen include the condensation products obtained from thiodiglycol per se and/or with other glycols, dicarboxylic acids, formaldehyde, aminocarboxylic acids, and/or amino alcohols. The products obtained are either mixed polythioethers, polythioether esters, or polythioether ester amides, depending on the co-components.

Optional polyacetals include but are not limited to the compounds which can be prepared from aldehydes, for example formaldehyde, and from glycols, such as diethylene glycol, triethylene glycol, ethoxylated 4,4'-(dihydroxy)diphenyl-dimethylmethane, and (1,6)-hexanediol. Polyacetals useful according to various non-limiting embodiments of the disclosure can also be prepared by polymerization of cyclic acetals.

Optional polyhydroxy polyesteramides and polyamines include, for example, the mainly linear condensation products obtained from saturated or unsaturated, polybasic carboxylic acids or anhydrides thereof, and from saturated or unsaturated, polyvalent amino alcohols, from diamines, or from polyamines, as well as mixtures thereof.

Optional monomers for the production of polyacrylates having hydroxyl functionality comprise acrylic acid, methacrylic acid, crotonic acid, maleic anhydride, 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, glycidyl acrylate, glycidyl methacrylate, 2-isocyanatoethyl acrylate, and 2-isocyanatoethyl methacrylate.

Mixtures of dihydroxy compounds can also be used.

Optional polyisocyanates for providing the hydrocarbon-based radical R2 include, for example, organic diisocyanates having a molecular weight ranging from about 100 to about 1500, such as about 112 to about 1000, or about 140 to about 400.

Optional diisocyanates are those chosen from the general formula $R_2(NCO)_2$, in which $R_2$ represents a divalent aliphatic hydrocarbon group comprising from about 4 to 18 carbon atoms, a divalent cycloaliphatic hydrocarbon group comprising from about 5 to 15 carbon atoms, a divalent araliphatic hydrocarbon group comprising from about 7 to 15 carbon atoms, or a divalent aromatic hydrocarbon group comprising from about 6 to 15 carbon atoms. Examples of the organic diisocyanates which may be chosen include, but are not limited to, tetramethylene diisocyanate, 1,6-hexamethylene diisocyanate, dodecamethylene diisocyanate, cyclohexane-1,3-diisocyanate and cyclohexane-1,4-diisocyanate, 1-isocyanato-3-isocyanatomethyl-3,5,5-trimethyl-cyclohexane (isophorone diisocyanate or IPDI), bis(4-isocyanatocyclohexyl)-methane, 1,3-bis(isocyanatomethyl)cyclohexane and 1,4-bis(isocyanatomethyl)cyclohexane and bis(4-isocyanato-3-methylcyclohexyl)methane. Mixtures of diisocyanates can also be used.

In at least certain embodiments, diisocyanates are chosen from aliphatic and cycloaliphatic diisocyanates. For example, 1,6-hexamethylene diisocyanate, isophorone diisocyanate, and dicyclohexylmethane diisocyanate, as well as mixtures thereof may be chosen.

The use of diols, for example low molecular weight diols, R3, may in at least certain embodiments allow a stiffening of the polymer chain. The expression "low molecular weight diols" means diols having a molecular weight ranging from about 50 to about 800, such as about 60 to 700, or about 62 to 200. They may, in various embodiments, contain aliphatic, alicyclic, or aromatic groups. In certain exemplary embodiments, the compounds contain only aliphatic groups. The diols that may be chosen may optionally have up to about 20 carbon atoms, and may be chosen, for example, from ethylene glycol, diethylene glycol, propane-1,2-diol, propane-1,3-diol, butane-1,4-diol, 1,3-butylene glycol, neopentyl glycol, butylethylpropanediol, cyclohexanediol, 1,4-cyclohexanedimethanol, hexane-1,6-diol, bisphenol A (2,2-bis(4-hydroxyphenyl)propane), hydrogenated bisphenol A (2,2-bis(4-hydroxycyclohexyl)-propane), and mixtures thereof. For example, R3 may be derived from neopentyl glycol.

Optionally, the low molecular weight diols may contain ionic or potentially ionic groups. Suitable low molecular weight diols containing ionic or potentially ionic groups may be chosen from those disclosed in U.S. Pat. No. 3,412,054. In various embodiments, compounds may be chosen from dimethylolbutanoic acid (DMBA), dimethylolpropionic acid (DMPA), and carboxyl-containing caprolactone polyester diol. If low molecular weight diols containing ionic or potentially ionic groups are chosen, they may, for example, be used in an amount such that less than about 0.30 meq of —COOH is present per gram of polyurethane in the polyurethane dispersion. In at least certain exemplary and non-limiting embodiments, the low molecular weight diols containing ionic or potentially ionic groups are not used.

Reaction product (ii) may be chosen from at least one chain extender according to the formula:

wherein R4 is chosen from alkylene or alkylene oxide radicals, said radicals not being substituted with ionic or potentially ionic groups.

Reaction product (ii) may optionally be chosen from alkylene diamines, such as hydrazine, ethylenediamine, propylenediamine, 1,4-butylenediamine and piperazine; and alkylene oxide diamines such as dipropylamine diethylene glycol (DPA-DEG available from Tomah Products, Milton, Wis.), 2-methyl-1,5-pentanediamine (Dytec A from DuPont), hexanediamine, isophoronediamine, and 4,4-methylenedi(cyclohexylamine), and the DPA-series of ether amines available from Tomah Products, Milton, Wis., including dipropylamine propylene glycol, dipropylamine dipropylene glycol, dipropylamine tripropylene glycol, dipropylamine poly(propylene glycol), dipropylamine ethylene glycol, dipropylamine poly(ethylene glycol), dipropylamine 1,3-propanediol, dipropylamine 2-methyl-1,3-propanediol, dipropylamine 1,4-butanediol, dipropylamine 1,3-butanediol, dipropylamine 1,6-hexanediol and dipropylamine cyclohexane-1,4-dimethanol, and mixtures thereof.

Reaction product (iii) may be chosen from at least one chain extender according to the formula:

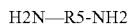

wherein R5 is chosen from alkylene radicals substituted with ionic or potentially ionic groups. In at least certain exemplary embodiments, the compounds may have an ionic or potentially ionic group and two isocyanate-reactive groups.

As used herein, ionic or potentially ionic groups may include groups comprising ternary or quaternary ammonium groups, groups convertible into such groups, carboxyl groups, carboxylate groups, sulphonic acid groups, and sulphonate groups. At least partial conversion of the groups convertible into salt groups of the type mentioned may take place before or during the mixing with water. Specific compounds include diaminosulphonates, such as for example the sodium salt of N-(2-aminoethyl)-2-aminoethanesulphonic acid (AAS) or the sodium salt of N-(2-aminoethyl)-2-aminopropionic acid.

In at least certain embodiments, R5 represents an alkylene radical substituted with sulphonic acid or sulphonate groups. By way of example only, the compound is chosen from sodium salts of N-(2-aminoethyl)-2-aminoethanesulphonic acid.

By way of non-limiting example, such latexes include, but are not limited to, aqueous polyurethane dispersions comprising a reaction product of a prepolymer comprising a dihydroxyl compound, a polyisocyanate, and a low molecular weight diol and at least two diamine compounds and wherein the composition is substantially free of triethanolamine stearate such as, for example, those sold under the BAYCUSAN® name by Bayer such as, for example, BAYCUSAN® C1000 (INCI name: Polyurethane-34), BAYCUSAN® C1001 (INCI name: Polyurethane-34), BAYCUSAN® C1003 (INCI name: Polyurethane-32), BAYCUSAN® C1004 (INCI name: Polyurethane-35) and BAYCUSAN® C1008 (INCI name: Polyurethane-48). In various exemplary embodiments, polyurethane latexes may be chosen from, but are not limited to, aqueous polyurethane dispersion of Isophthalic Acid/Adipic Acid/Hexylene Glycol/Neopentyl glycol/Dimethylolpropanoic Acid/Isophorone Diisocyanate copolymer (INCI name: Polyurethane-1, such as LUVISET® P.U.R, BASF), aliphatic polyurethane and aliphatic polyester polyurethane (such as the NEOREZ® series, DSM, such as NEOREZ® R989, INCI name: Polycarbamyl Polyglycon Ester).

Specific non-limiting examples of hard and soft latex film-forming polymers are provided in the tables below.

Hard Latex Film-Forming Polymers

| Trade Name | Description |
|---|---|
| SYNTRAN 5905 | Styrene/Acrylates Copolymer |
| LUVIFLEX SOFT | Acrylates copolymer |
| LUVIMER MAE | Acrylates copolymer |
| NEOCRYL A-2091 | Styrene acrylic copolymer dispersion |
| ACUDYNE 180 | Acrylates/Hydroxyesters Acrylate Copolymer |
| FIXATE SUPERHOLD | Polyacrylate-2 Crosspolymer |
| ACULYN 33 | Acrylates Copolymer |
| ACUDYNE LT -120 | Acrylates/C1-2 succinates/hydroxyacrylates copolymer |
| SALCARE SC81 | Acrylates Copolymer |
| SYNTRAN KL-219CG | Ammonium Acrylates copolymer and sodium lauryl sulfate and disodium deceth-6 sulfosucinate |
| ACUDYNE SHINE | Acrylic copolymer |
| ACUDYNE BOLD | Acyrlic copolymer |
| VISCOPHOBE DB 1000 | Polyacrylate-3 |
| NEOCRYL XK 102 | Hydroxyl functional acrylic emulsion |
| DERMACRYL AQF | Acrylic Copolymer |
| BALANCE CR | Acrylates copolymer |
| ACULYN 28 | Acrylates/beheneth-25 methacrylate copolymer |
| SYNTRAN PC 5620 | Acrylates copolymer and butylene glycol and sodium laureth sulfate |
| SYNTRAN PC 5205 | polyacrylate-15 and polyacrylate-17 |
| SYNTRAN 5100 CG | polyacrylate-21 and acrylates/dmethylaminoethyl methacrylates |
| SYNTRAN EX 56 | Acrylic copolymer |
| ACUDYNE DHR | Acrylates/Hydroxyesters Acrylate Copolymer |
| SYNTRAN EX 53 | Acrylic copolymer |
| ACULYN 88 POLYMER | Acrylates/steareth-20 methacrylate crosspolymer |
| VINYLSOL 1086 WP | Ammonium Acrylates copolymer |
| JONCRYL 77 | Styrene/Acrylates Copolymer |
| DAITOSOL 3000 VP3 | Aqueous emulsion of copolymer of methyl methacrylate butyl acrylate and methacrylic acid |
| NEOCRYL XK 16 | Self-crosslinking acrylic emulsion |
| DAITOSOL 3000 SLPN | Aqueous emulsion of copolymer of methyl methacrylate butyl acrylate and methacrylic acid |
| SYNTRAN 5760 | Styrene/acrylates/ammonium methacrylate copolymer and sodium lauryl sulfate and carylyl glycol |
| RHOPLEX P376 | Acrylic copolymer emulsion |
| SYNTRAN 5760 | Styrene/acrylates/ammonium methacrylate copolymer |
| NEOCRYL A45 | Acrylates copolymer |
| DAITOSOL 5000STY | Alkyl acrylate/styrene copolymer |
| VINYLSOL 2140 L | Acrylate/VA copolymer |
| NEOREZ R-989 | Polycarbamyl Polyglycol Ester |

Soft Latex Polymers (acrylate polymers)

| Tradename | Description |
|---|---|
| DERMACRYL C | Acrylic/Acrylate Copolymer |
| DAITOSOL 5000 SJ | Acrylate/Ethylhexyl Acrylate copolymer |
| DAITOSOL 4000 SJT | Acrylates/ethylhexyl acrylate copolymer |
| DAITOSOL 5000AD | Acrylate copolymer |
| EPITEX 66 POLYMER | Acrylic copolymer |
| SYNTRAN PC 5775 | Acrylic copolymer water based dispersion |
| HYBRIDUR 875 | Polyurethane-2 (and) polymethyl methacrylate |

Soft Latex Polymers (polyurethane polymers)

| Tradename | Description |
|---|---|
| BAYCUSAN C 1008 | Polyurethane-48 |
| BAYCUSAN C 1004 | Polyurethane-35 |
| BAYCUSAN C 1001 | Polyurethane-34 |
| BAYCUSAN C 1000 | Polyurethane-32 |

Implementation of the present disclosure is provided by way of the following examples. The examples serve to illustrate the technology without being limiting in nature.

Example 1

Compatibility of the Latex Film-Forming Polymers

The compatibility of individual latex film-forming polymers and combinations of hard and soft latex film-forming polymers in organic solvent (ethanol) was determined. A solution was obtained by mixing a 100 g ethanol with 2 g of latex film-forming polymers at room temperature for 1 hr. The compatibility of the latex film-forming polymers was visually assessed based on the uniformity and clarity of the solution, precipitation, and/or separation.

| | 100 VOC | 95 VOC* | 80 VOC** |
|---|---|---|---|
| Single Soft Latex Film-Forming Polymer | | | |
| Polyurethane-34 (BAYCUSAN C1001) | x | √ | √ |
| Acrylates/Ethylhexyl Acrylate Copolymer (DAITOSOL 5000 AD) | √ | √ | √ |
| Single Hard Latex Film-Forming Polymer | | | |
| Acrylates Copolymer (BALANCE CR) | √ | √ | √ |
| Polyacrylates-2 Crosspolymer (FIXATE SUPERHOLD) | √ | √ | √ |
| Acrylates/Hydroxyesters Acrylates Copolymer (ACUDYNE 180) | √ | √ | √ |
| Styrene-Acrylates Copolymer (JONCRYL 77) | x | x | √ |
| Combination of Hard & Soft Latex Film-Forming Polymer | | | |
| Acrylates Copolymer (BALANCE CR) & Polyurethane-34 (BAYCUSAN C1001) | x | √ | √ |
| Polyacrylates-2 Crosspolymer (FIXATE SUPERHOLD) & Polyurethane-34 (BAYCUSAN C1001) | x | √ | √ |
| Acrylates/Hydroxyesters Acrylates Copolymer (ACUDYNE 180) & Polyurethane-34 (BAYCUSAN C1001) | x | √ | √ |

-continued

|  | 100 VOC | 95 VOC* | 80 VOC** |
|---|---|---|---|
| Acrylates Copolymer (BALANCE CR) & Acrylates/ Ethylhexyl Acrylate Copolymer (DAITOSOL 5000 AD) | √ | √ | √ |
| Polyacrylates-2 Crosspolymer (FIXATE SUPERHOLD) & Acrylates/Ethylhexyl Acrylate Copolymer (DAITOSOL 5000 AD) | √ | √ | √ |
| Acrylates/Hydroxyesters Acrylates Copolymer (ACUDYNE 180) & Acrylates/Ethylhexyl Acrylate Copolymer (DAITOSOL 5000 AD) | √ | √ | √ |

*contains 5% of water
**contains 20% of water
"√" Stands for good compatibility; the mixture is clear and uniform without precipitation/separation.
"X" Stands for incompatibility; the mixture is cloudy with precipitation/separation.

Example 2

Quality and Curl Retention of Films

The quality of films formed from a combination of a hard and a soft latex film-forming polymer, with and without a plasticizer/coalescing agent was determined. The films were obtained by using a 25 mm cube film applicator, 75 um gap sizes. The films were formed on a clean glass plate at 40% controlled humidity. The film quality was graded on a scale of 1-3 (3 being best), based on the clarity and uniformity of the films.

To determine the High Humidity Curl Retention (HHCR), the film-forming composition (0.5 g solution/g hair) was applied to regular bleached hair swatches (from HIP, 14.5 cm long, about 0.5 g). The hair was combed until the solution was uniformly distributed over the hair surface. The treated hair was then rolled onto a spiral rod (0.5 in diameter) and allowed to dry at room temperature overnight. The next day, the hair was removed from the rods and placed in a humidity chamber at 90% RH, 25° C. for 24 hours. The Curl Retention was calculated as: (Lo−Lf)/(Lo−Li)×100, wherein Lo=Fully extended hair length (14.5 cm), Li=Initial coiled hair length before humidity exposure, and Lf=Final hair length after 24 hr exposure. The HHCR was compared with the HHCR of a commercially available benchmark hair spray (having an HHCR of 49).

The resulting quality of the films and the percent curl retention are reported in the tables below.

| Hard Latex Film-Former Polyacrylates-2 Crosspolymer (FIXATE SUPERHOLD) | Soft Latex Film-Former Acrylates/Ethylhexyl Acrylate Copolymer (DAITOSOL 5000 AD) | Plasticizer/ Coalescent (Tributyl Citrate) | EtOH | Visc. at 23° C. | HHCR (%) | Film Quality (1-3) |
|---|---|---|---|---|---|---|
| 5.83 | 0 | 0 | qs to 100 wt. % |  | 61 | 1 |
| 5.83 | 0 | 0.5 | qs to 100 wt. % |  | 72 | 2 |
| 0 | 5.83 | 0 | qs to 100 wt. % |  | 32 | 2 |
| 0 | 5.83 | 0.5 | qs to 100 wt. % |  | 33 | 2 |
| 1.83 | 4 | 0 | qs to 100 wt. % | <70 cP | 57 | 1 |
| 1.83 | 4 | 0.5 | qs to 100 wt. % | 26 cP | 83 | 2 |
| Commercially Available Benchmark Hairspray |  |  |  |  | 49 |  |

| Hard Latex Film-Former Polyacrylates-2 Crosspolymer (FIXATE SUPERHOLD) | Soft Latex Film-Former Polyurethane-34 (BAYCUSAN C1001) | Plasticizer/ Coalescent (Tributyl Citrate) | Water | EtOH | HHCR (%) | Film Quality (1-3) |
|---|---|---|---|---|---|---|
| 5.83 | 0 | 0 | 5 | qs to 100 wt. % | 61 | 1 |
| 5.83 | 0 | 0.3 | 5 | qs to 100 wt. % | 72 | 2 |
| 0 | 5.4 | 0 | 5 | qs to 100 wt. % | 51 | 2 |
| 0 | 5.4 | 0.3 | 5 | qs to 100 wt. % | 40 | 2 |

-continued

| Hard Latex Film-Former Polyacrylates-2 Crosspolymer (FIXATE SUPERHOLD) | Soft Latex Film-Former Polyurethane-34 (BAYCUSAN C1001) | Plasticizer/ Coalescent (Tributyl Citrate) | Water | EtOH | HHCR (%) | Film Quality (1-3) |
|---|---|---|---|---|---|---|
| 5.25 | 0.15 | 0 | 5 | qs to 100 wt. % | 59 | 1 |
| 5.25 | 0.15 | 0.3 | 5 | qs to 100 wt. % | 74 | 2 |
| Commercially Available Benchmark Hairspray | | | | | 49 | |

The results indicate that/coalescing agents improve the quality of the in terms of clarity and uniformity. Furthermore, plasticizers/coalescing agents improved the high humidity curl retention (HHCR) for both the single latex films and the combination latex films. Furthermore, the combination latex films provided considerably more curl retention (HHCR) than the commercial benchmark product.

Example 3

Latex Hairspray

| | INCI US Name | wt. % Hair-Spray Composition (Juice) | wt. % (With Propellant) |
|---|---|---|---|
| Soft Latex Film-Forming Polymer | ACRYLATES COPOLYMER * | 4 | 1.6 |
| Hard Latex Film-Forming Polymer | POLYACRYLATE-2 CROSSPOLYMER ** | 1.8 | 0.7 |
| Organic Solvent | ETHANOL | 86 | 34.1 |
| Water | WATER | 8 | 3.2 |
| Coalescing Agent and/or Plasticizer | TRIBUTYL CITRATE | 0.5 | 0.2 |
| Fragrance | OPTIONAL COMPONENT | 0-2 | 0-2 |
| Propellant | DIMETHYL ETHER | — | 60 |
| | | 100 | 100 |

* Acrylic/Acrylates Copolymer (INCI name: Acrylates Copolymer, such as Daitosol 5000AD, Daito Kasei Kogyo)
** PEG/PPG-23/6 Dimethicone Citraconate/C10-30 Alkyl PEG-25 Methacrylate/Acrylic Acid/Methacrylic Acid/Ethyl Acrylate/Trimethylolpropane PEG-15 Triacrylate copolymer (INCI: Polyacrylate-2 Crosspolymer; Fixate Superhold™ by Lubrizol)

The results indicate that with the help of plasticizers and/or coalescents, the quality of so formed films is improved in terms of clarity and uniformity. Furthermore, the high humidity curl retention for the single latex and the latex association also improved with the plasticizers/coalescents.

The above examples show that with the addition of plasticizers and coalescents, more robust films with better styling properties are obtained. These results offer us the ability and the tools to control and to improve the resistance/resiliency against high humidity and deformation produced by grooming, bodily motion, wind, etc. . . . in hair styling of men and women with short to long hair, straight to curly hair.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

The terms "a," "an," and "the" are understood to encompass the plural as well as the singular.

The expression "one or more" means "at least one" and thus includes individual components as well as mixtures/combinations.

Other than in the operating examples, or where otherwise indicated, all numbers expressing quantities of ingredients and/or reaction conditions are to be understood as being capable of modified with the term "about," meaning within +/−5% of the indicated number.

All percentages, parts and ratios herein are based upon the total weight of the compositions of the present invention, unless otherwise indicated.

"Volatile", as used herein, means having a flash point of less than about 100° C.

"Non-volatile", as used herein, means having a flash point of greater than about 100° C.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

Other than in the operating examples, or where otherwise indicated, all numbers expressing quantities of ingredients and/or reaction conditions are to be understood as being modified in all instances by the term "about," meaning within +/−5% of the indicated number.

The term "substantially free" or "essentially free" as used herein means that there is less than about 5% by weight of a specific material added to a composition, based on the total weight of the composition. Nonetheless, the compositions may include less than about 1 wt. %, less than about 0.5 wt. %, less than about 0.1 wt. %, or none of the specified material.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A hair styling composition comprising:
   about 1 to about 6 wt. % of acrylates copolymer;
   about 0.5 to about 4 wt. % of polyacrylate-2 crosspolymer;
   about 5 to about 15 wt. % of water;
   at least 80 wt. % to about 95 wt. % of an alcohol selected from ethanol, isopropyl alcohol, butanol, and a mixture thereof; and
   about 0.1 to about 3 wt. % of tributyl citrate;
      wherein the weight percentages are based on the total weight of the hair styling composition, and the hair styling composition has a shear viscosity of up to about 70 cP at 23° C.

2. A non-aerosol hair styling product comprising a spray bottle, the spray bottle containing a mechanical spray pump device and a hair styling composition of claim 1.

3. An aerosol hair styling product comprising a canister, the canister containing a propellant and a hair styling composition of claim 1.

4. An aerosol hair styling product of claim 3, wherein the propellant is selected from dimethyl ether, propane, n-butane, isobutene, and a mixture thereof.

5. An aerosol hairspray product comprising a canister, the canister containing:
   a vapor phase comprising a propellant; and
   a juice phase comprising a hair styling composition comprising:
      about 1 to about 6 wt. % of acrylates copolymer;
      about 0.5 to about 4 wt. % of polyacrylate-2 crosspolymer;
      5 to about 15 wt. % of water;
      at least 80 wt. % to about 95 wt. % of an alcohol selected from ethanol, isopropyl alcohol, butanol, and a mixture thereof; and
      about 0.1 to about 3 wt. % of tributyl citrate;
         wherein the weight percentages are based on the total weight of the juice phase.

6. A method for styling hair comprising applying to hair the hair styling composition of claim 1.

* * * * *